(12) United States Patent  
Narisada

(10) Patent No.: US 6,979,570 B2  
(45) Date of Patent: Dec. 27, 2005

(54) PARTICLE ANALYZER AND PARTICLE ANALYZING METHOD

(75) Inventor: Noriyuki Narisada, Akashi (JP)

(73) Assignee: Sysmex Corporation, Kobe (JP)

( * ) Notice: Subject to any disclaimer, the term of this patent is extended or adjusted under 35 U.S.C. 154(b) by 45 days.

(21) Appl. No.: 10/202,885

(22) Filed: Jul. 26, 2002

(65) Prior Publication Data

US 2003/0032193 A1 Feb. 13, 2003

(30) Foreign Application Priority Data

Jul. 26, 2001 (JP) .............................. 2001-226383

(51) Int. Cl.$^7$ .......................................... G01N 33/48
(52) U.S. Cl. .................... 436/63; 436/10; 436/164; 436/172; 422/73; 422/82.05; 422/82.08; 422/82.09; 702/19; 702/21; 702/29
(58) Field of Search ............................ 436/63, 10, 164, 436/172; 422/73, 82.05, 82.08, 82.09; 435/2, 435/29, 39; 702/19, 21, 26, 29

(56) References Cited

U.S. PATENT DOCUMENTS

| | | | | |
|---|---|---|---|---|
| 5,555,198 A | * | 9/1996 | Asano | ..................... 382/128 |
| 5,677,183 A | | 10/1997 | Takarada et al. | |
| 5,690,105 A | * | 11/1997 | Shibata et al. | .............. 600/300 |
| 5,731,867 A | * | 3/1998 | Katayama | ..................... 356/73 |
| 5,824,269 A | * | 10/1998 | Kosaka et al. | ................. 422/73 |
| 6,118,522 A | * | 9/2000 | Kanai et al. | ................... 356/73 |
| 6,246,786 B1 | * | 6/2001 | Nishikiori et al. | ........... 382/134 |
| 6,365,106 B1 | * | 4/2002 | Nagai | ........................... 422/73 |
| 6,472,168 B2 | * | 10/2002 | Matsumoto et al. | ........ 435/40.5 |
| 6,525,807 B1 | * | 2/2003 | Morikawa et al. | ............. 356/72 |

FOREIGN PATENT DOCUMENTS

| | | |
|---|---|---|
| JP | 6-3252 A | 1/1994 |
| JP | 11-30580 * | 2/1999 |

* cited by examiner

Primary Examiner—Maureen M. Wallenhorst  
(74) Attorney, Agent, or Firm—Birch, Stewart, Kolasch & Birch, LLP

(57) ABSTRACT

A particle analyzer includes a detecting section for detecting respective characteristic parameters of a plurality of particles, a distribution map preparing section for preparing at least two kinds of two-dimensional frequency distribution maps of the particles by using the detected characteristic parameters, a classifying section for classifying the particles into particle clusters on the two kinds of distribution maps, a calculating section for calculating and comparing the respective numbers of particles in the particle clusters containing particles of common kind to the two kinds of distribution maps, and a judging section for judging a classification error on the distribution maps based on a comparison result.

10 Claims, 7 Drawing Sheets

PARTICLE ANALYZER AND PARTICLE ANALYZING METHOD

CROSS-REFERENCE TO RELATED APPLICATION

This application is related to Japanese Patent Application No. 2001-226383 filed on Jul. 26, 2001, whose priority is claimed under 35 USC §119, the disclosure of which is incorporated by reference in its entirety.

BACKGROUND OF THE INVENTION

1. Field of the Invention

The present invention relates to a particle analyzer and a particle analyzing method. In particular, it relates to a particle analyzer for preparing two-dimensional frequency distribution maps (scattergrams) by using characteristic parameters of particles and classifying the particles indicated on the distribution maps to determine the kind and the number of the particles.

2. Description of Related Art

In the field of the particle analyzer of this kind, conventionally known is a particle analyzer which presets a plurality of regions on a two-dimensional frequency distribution map and calculates degrees of attribution of particles indicated on the distribution map with respect to the preset regions to classify the particles based on the calculated attribution degrees (see Japanese Unexamined Patent Publication No. Hei 6 (1994)-3252, for example). Moreover, known is a method for classifying and counting leukocytes in which the leukocytes are classified into five groups by using two kinds of reagents (see U.S. Pat. No. 5,677,183, for example).

However, if the conventional particle analyzer is used to analyze blood cells contained in blood, particle clusters which will appear on the two-dimensional frequency distribution map may be shifted when characteristic parameters used for preparing the distribution map are varied depending on some factors, e.g., the kind and amount of a reagent for diluting the blood to be analyzed, contamination of a detector for detecting electric or optical data from the blood cells, or variation in amplification degree of an electric circuit for converting the detected data into an electric signal to obtain the characteristic parameters. Therefore, accurate classification cannot be carried out and false analysis results may be obtained.

SUMMARY OF THE INVENTION

Under the above-described circumstances, the present invention has been achieved to provide a particle analyzer capable of judging a classification error when the classification is carried out falsely.

The present invention provides a particle analyzer comprising a detecting section for detecting respective characteristic parameters of a plurality of particles, a distribution map preparing section for preparing at least two kinds of two-dimensional frequency distribution maps of the particles by using the detected characteristic parameters, a classifying section for classifying the particles into particle clusters on the two kinds of distribution maps, a calculating section for calculating and comparing the respective numbers of particles in the particle clusters containing particles of common kind to the two kinds of distribution maps, and a judging section for judging a classification error on the distribution maps based on a comparison result.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
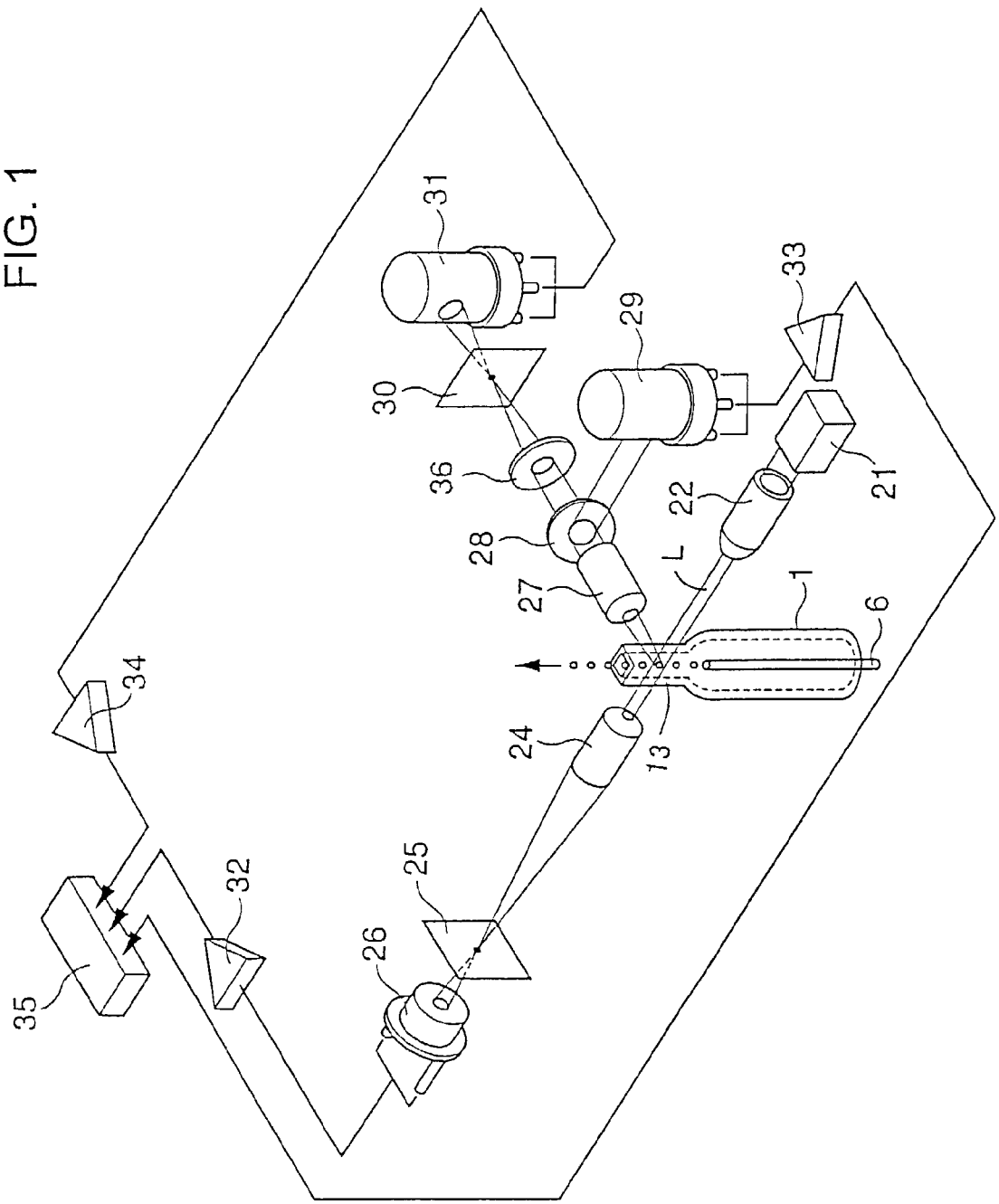
FIG. 1 is a perspective view illustrating an optical system according to an embodiment of the present invention.

A particle analyzer of the present invention includes a detecting section for detecting respective characteristic parameters of a plurality of particles; a distribution map preparing section for preparing at least two kinds of two-dimensional frequency distribution maps of the particles by using the detected characteristic parameters; a classifying section for classifying the particles into particle clusters on the two kinds of distribution maps; a calculating section for calculating and comparing the respective numbers of common particles classified on the two kinds of distribution maps; and a judging section for judging a classification error on the distribution maps based on a comparison result.

According to the present invention, particles to be analyzed include material components mainly contained in body fluids such as blood and urine. However, they may be particles of inorganic or organic materials for industrial use.

The detecting section according to the present invention may be, for example, a flow cytometer, i.e., an apparatus equipped with a flow cell for flowing a particle-containing fluid sheathed with a sheath liquid and an optical element for detecting characteristic parameters from the particles in the particle-containing fluid.

In this case, the characteristic parameters to be detected may be optical data based on forward scattered light, side scattered light and fluorescent light (e.g., side fluorescent light).

In the flow cytometer, the optical element performs photoelectric conversion of the optical data to generate a pulse signal in accordance with the characteristics of the particles. The characteristic parameters can be obtained by assuming a peak level of the pulse signal as a light intensity or a time period during which the pulse signal exceeds a predetermined threshold value as a pulse width. That is, the characteristic parameters may be forward scattered light data including a forward scattered light intensity and a forward scattered light pulse width, side scattered light data including a side scattered light intensity and a side scattered light pulse width, and side fluorescent light data including a side fluorescent light intensity and a side fluorescent light pulse width.

If the flow cytometer is used as the detecting section, the two-dimensional frequency distribution maps prepared by the distribution map preparing section may be that based on the side scattered light intensity and the side fluorescent light intensity, that based on the side scattered light intensity and the forward scattered light intensity, that based on the side fluorescent light intensity and the forward scattered light intensity and that based on the side fluorescent light intensity and the forward scattered light intensity.

The classifying section may classify the particles on the distribution maps into clusters by a known technique, for example, that described in Japanese Unexamined Patent Publication No. Hei 6 (1994)-3252.

The classifying section, the calculating section and the judging section according to the present invention may be integrated into a microcomputer or a personal computer including a CPU, a ROM and a RAM.

If the detecting section is constituted of the flow cytometer and the characteristic parameters are the forward scattered light intensity, the side scattered light intensity and the side fluorescent light intensity, the two kinds of two-dimensional frequency distribution maps may include a first distribution map based on the side fluorescent light intensity and the forward scattered light intensity and a second distribution map based on the side scattered light intensity and the side fluorescent light intensity.

In this case, if the particles to be detected are blood cells, the classifying section may classify leukocytes (neutrophils, basophils, eosinophils, lymphocytes and monocytes) on the first distribution map and neutrophils, basophils and eosinophils, which are subclasses of the leukocytes, on the second distribution map.

At this time, the calculating section may calculate the number N of the leukocytes (neutrophils, basophils, eosinophils, lymphocytes and monocytes) on the first distribution map and the sum M of the numbers of the neutrophils, basophils and eosinophils on the second distribution map to compare M with N, and the judging section may judge a classification error on the first distribution map when N<M.

In another aspect, the present invention provides a particle analyzer comprising a quantifying section for quantifying a specimen containing particles, a sample preparing section for preparing a first sample and a second sample by using the quantified specimen, a detecting section for detecting a plurality of characteristic parameters from particles in the first and second samples, a distribution map preparing section for preparing first and second two-dimensional frequency distribution maps based on the detected characteristic parameters of the first and second samples, respectively, a classifying section for classifying particles indicated on the distribution maps into particle clusters, a calculating section for calculating and comparing the respective numbers of particles in the particle clusters containing particles of common kind to the first and second distribution maps, a judging section for judging a classification error on the distribution maps by comparison results obtained by the calculating section.

Hereinafter, the present invention is detailed by way of an embodiment with reference to FIGS. 1 to 9 of the drawings.

Components which are common in the figures are indicated with common reference numerals.

Structure of Particle Analyzer

In this embodiment, the particle analyzer of the invention is used as a blood analyzer.

FIG. 1 is a perspective view illustrating an optical system, i.e., a flow cytometer of the blood analyzer. Referring to FIG. 1, a nozzle 6 discharges a sample liquid containing blood cells toward an orifice 13 in a sheath flow cell 1. A laser beam L output from a laser diode 21 irradiates the orifice 13 of the sheath flow cell 1 via a collimate lens 22. Forward scattered light emitted from the blood cells passing through the orifice 13 enters a photodiode 26 via a condenser lens 24 and a pinhole plate 25.

On the other hand, side scattered light emitted from the blood cells passing through the orifice 13 enters a photomultiplier tube 29 via a condenser lens 27 and a dichroic mirror 28. Further, side fluorescent light emitted from the blood cells passing through the orifice 13 enters a photomultiplier tube 31 via the condenser lens 27, the dichroic mirror 28, a filter 36 and a pinhole plate 30.

A forward scattered light signal output from the photodiode 26, a side scattered light signal output from the photomultiplier tube 29 and a side fluorescent light signal output from the photomultiplier tube 31 are amplified by amplifiers 32, 33 and 34, respectively, and input to an analysis section 35.

Figure 2:
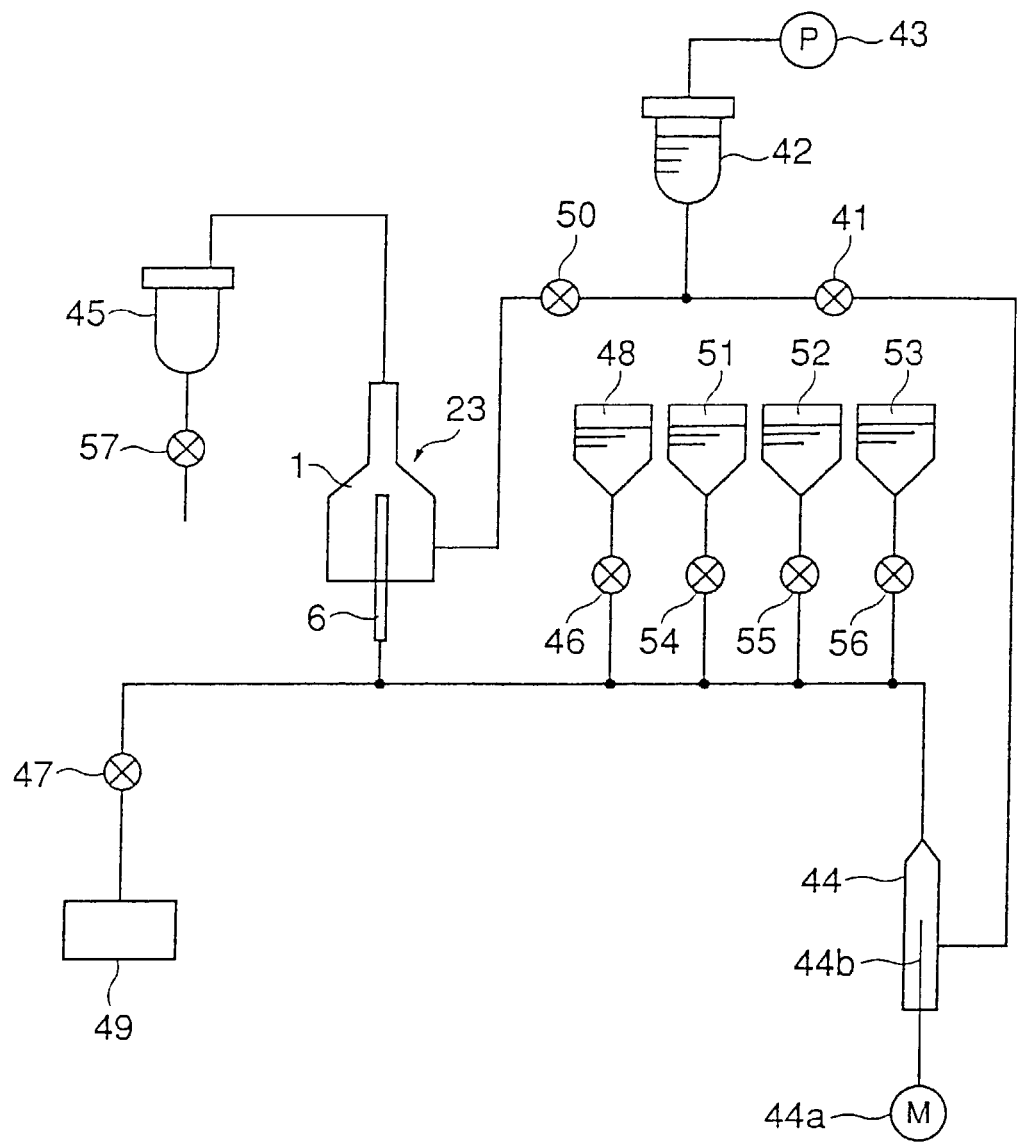
FIG. 2 is a block diagram illustrating a fluid system according to the embodiment of the present invention.

FIG. 2 is a block diagram illustrating a fluid system of the blood analyzer shown in FIG. 1. First, in a washing process, valves 41 and 50 are opened to feed a sheath liquid out of a sheath liquid chamber 42 under a positive pressure applied by a pressurizing device 43. Then, the sheath liquid passes through the valve 41, a quantifying syringe 44 and a nozzle 6 to a drain chamber 45. The sheath liquid also passes through the valve 50 and the sheath flow cell 1 to the drain chamber 45. The valves 41 and 50 are closed after a predetermined period of time. Thus, the quantifying syringe 44, the nozzle 6, the sheath flow cell 1 and paths connecting them are washed with the sheath liquid.

In a measurement process, valves 46 and 47 are opened to suck a blood-containing sample liquid under a negative pressure applied by a suction device 49 out of a reaction chamber 48 in which the sample liquid is reacted with a reagent. When the path between the valve 46 and the nozzle 6 is filled with the sample liquid, the valves 46 and 47 are closed. Then, the valve 50 is opened, thereby the sheath liquid is fed from the sheath liquid chamber 42 to the sheath flow cell 1 under the positive pressure applied by the pressurizing device 43 and drained into the drain chamber 45.

When the valve 41 is opened, the pressure applied by the pressurizing device 43 is transmitted to the tip of the nozzle 6 via the quantifying syringe 44. Thereby, the pressure of the sheath liquid outside the nozzle and that of the sheath liquid inside the nozzle are balanced at the tip of the nozzle 6. When a piston 44b of the quantifying syringe 44 is driven by a motor 44a in this state, the sample liquid existing between the valve 46 and the nozzle 6 is easily discharged from the nozzle 6 to the orifice 13 and narrowed by the sheath liquid to pass through the orifice 13. The sample liquid is then drained into the drain chamber 45 together with the sheath liquid.

Then, the piston 44b of the quantifying syringe 44 is stopped to finish the measurement process.

Subsequently, the motor 44a is driven in a reverse direction to put the piston 44b back, thereby the quantifying syringe 44 returns to an initial state. During this procedure, the valves 41 and 50 are opened so that the above-mentioned washing process is carried out to get ready for the next measurement process.

The sample liquids contained in the other reaction chambers 51, 52 and 53, respectively, are also measured in sequence by opening and closing valves 54, 55 and 56 in the same manner as the above-described process.

A valve 57 functions to empty the drain chamber 45, so that it is opened and closed as needed.

Figure 3:
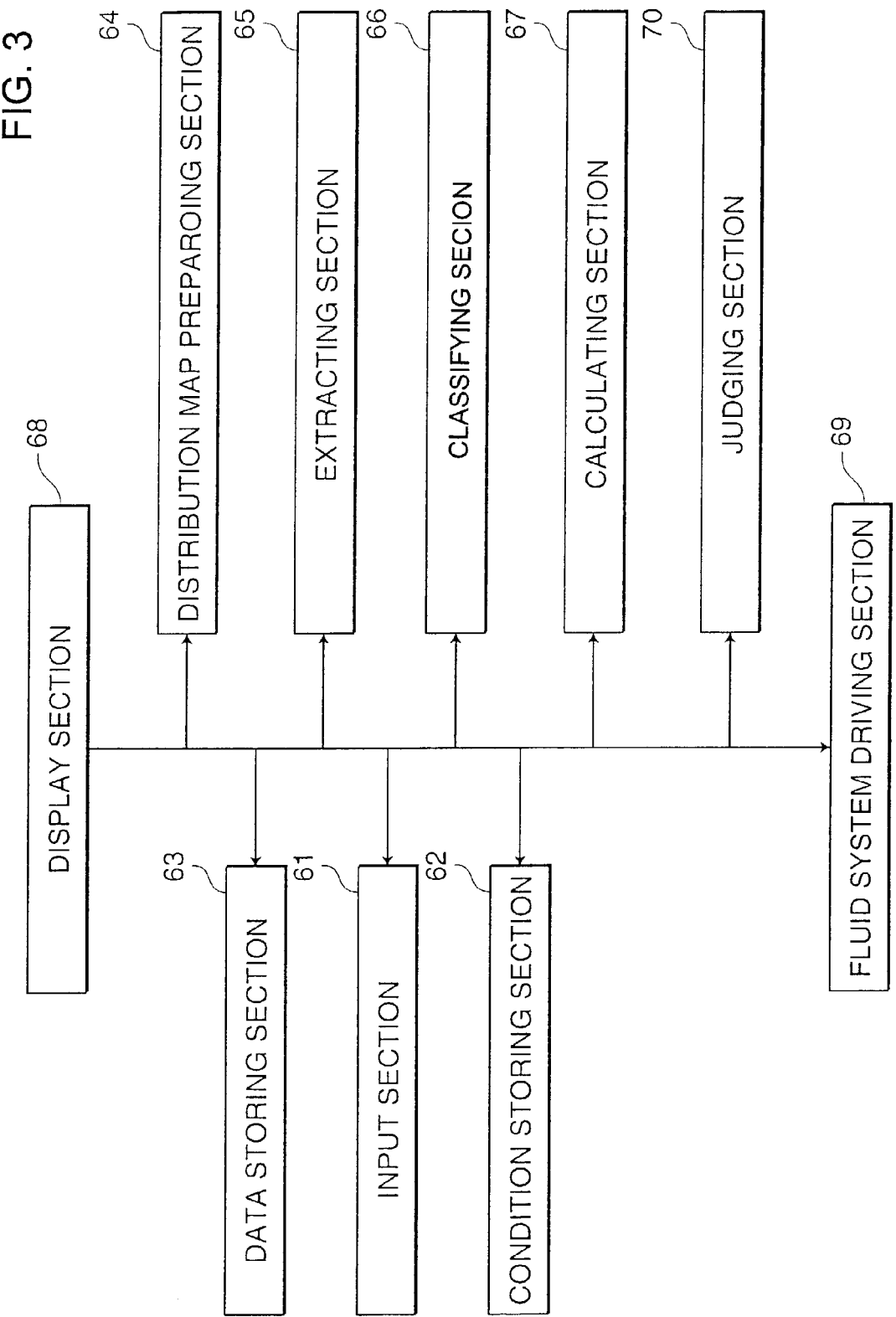
FIG. 3 is a block diagram illustrating a structure of an analysis section according to the embodiment of the present invention.

FIG. 3 is a block diagram illustrating the structure of the analysis section 35 shown in FIG. 1. Referring to FIG. 3, an input section 61 inputs data for previously setting up conditions such as numeric values and regions. For example, the input section 61 is a keyboard or a mouse.

A condition storing section 62 stores the given conditions and a data storing section 63 stores optical data obtained from the signals output from the photodiode 26 and the photomultiplier tubes 29 and 31. A distribution map preparing section 64 prepares a two-dimensional frequency distribution map based on the optical data stored in the data storing section 63, i.e., two parameters out of a forward scattered light intensity (Fsc), a side scattered light intensity (Ssc) and a side fluorescent light intensity (Sfl). An extracting section 65 extracts coordinates and regions from the distribution map prepared by the distribution map preparing section 64.

A classifying section 66 determines classification regions of particles on the distribution map prepared by the distribution map preparing section 64. A calculating section 67 counts the number of the particles in the classification regions and compares count results. Further, a judging section 70 judges a classification error on the distribution map by comparison results. The calculation results obtained by the calculating section 67 and the judgment results obtained by the judging section 70 are displayed in a display section 68 together with the distribution map prepared by the distribution map preparing section 64. Further, a fluid system driving section 69 drives the valves 41, 46, 47, 50, 54, 55, 56 and 57 and the motor 44a shown in FIG. 2. The analysis section 35 is constituted by a personal computer.

Preparation of Two-dimensional Frequency Distribution Maps

Figure 8:
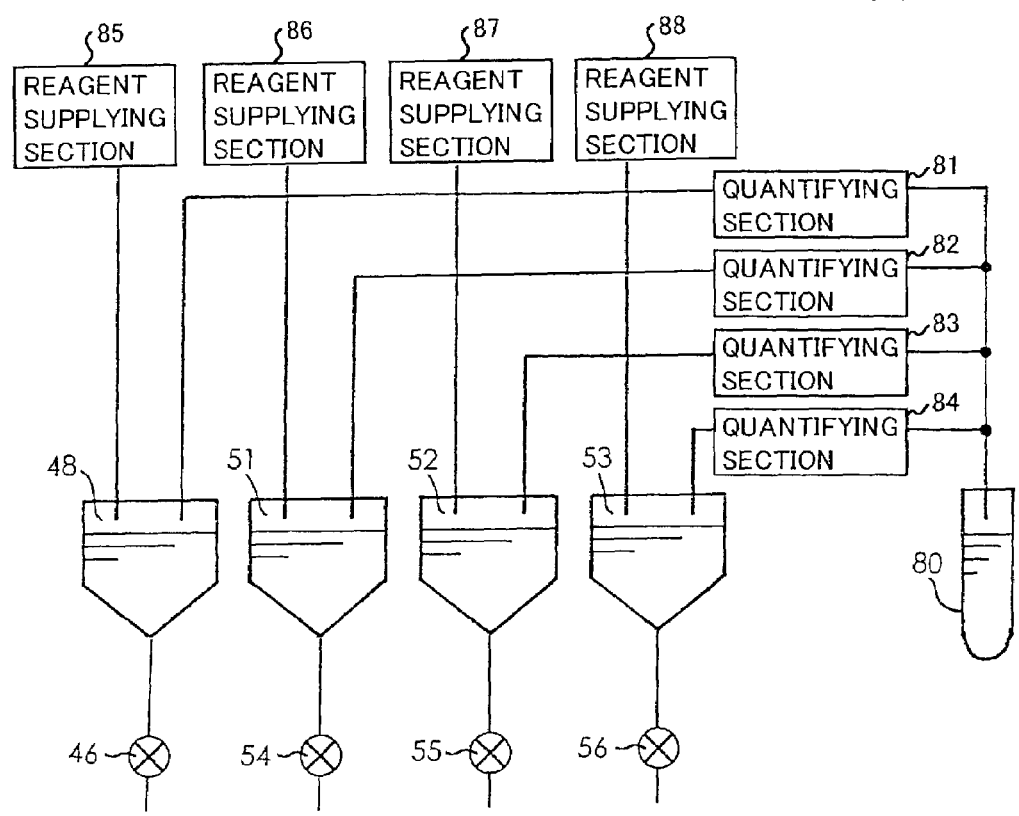
FIG. 8 is a detailed block diagram illustrating a major part of FIG. 2.

FIG. 8 is a detailed block diagram illustrating a major part of FIG. 2. FIG. 8 shows a sample container, quantifying sections and reagent supply sections, which are not shown in FIG. 2, in order to explain processes of preparing samples to be measured.

As shown in FIG. 8, blood (a single specimen) is sucked out of a sample container 80 and the required amount thereof is quantified by quantifying sections 81 to 84, respectively. The quantified blood are distributed into the reaction chambers 48, 51, 52 and 53, respectively. That is, the blood quantified for measurement in a nucleated erythrocyte measurement mode is distributed into the reaction chamber 48, that quantified for measurement in a leukocyte/basophil measurement mode is distributed into the reaction chamber 51, that quantified for measurement in a leukocyte 4-part differential measurement mode is distributed into the reaction chamber 52, and that quantified for measurement in a reticulocyte measurement mode is distributed into the reaction chamber 53. Then, predetermined reagents are supplied to the reaction chambers 48, 51, 52 and 53 from reagent supplying sections 85 to 88 to react the blood with the reagents, respectively. Thus, four samples corresponding to the measurement modes are prepared from the single blood specimen and measured in sequence by the sheath flow cell 1.

That is, when the above four measurement modes are input at the input section 61 (FIG. 3), each measurement mode is carried out as follows.

Nucleated Erythrocyte Measurement Mode

In this measurement mode, blood of 18 $\mu$l and Stromatolyzer NR hemolytic agent (manufactured by Sysmex Corporation) of 882 $\mu$l are introduced in the reaction chamber 48. Then, Stromatolyzer NR fluorescent stain solution (manufactured by Sysmex Corporation) of 18 $\mu$l is added. The reaction is continued in this state for about 7 seconds to hemolyze erythrocytes and stain leukocytes and nucleated erythrocytes.

Figure 4:
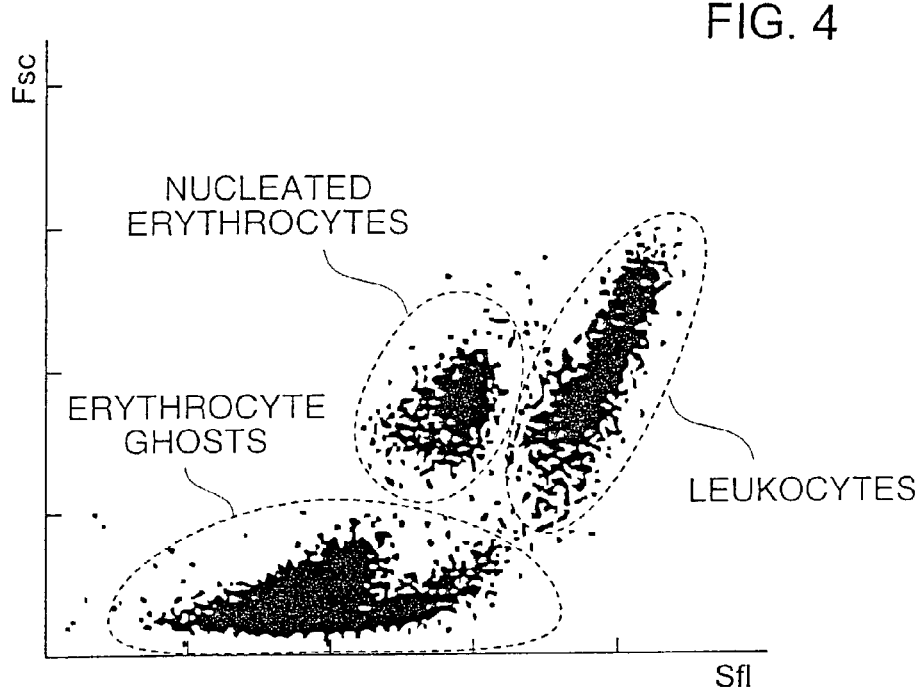
FIG. 4 is an example of a distribution map according to the embodiment of the present invention.

The thus treated sample is discharged from the nozzle 6 by the quantifying syringe 44. Among data obtained by the optical measurement, a side fluorescent light intensity (Sfl) and a forward scattered light intensity (Fsc) are used to prepare a two-dimensional frequency distribution map of FIG. 4. In FIG. 4, the nucleated erythrocytes and the leukocytes are classified into respective clusters.

Leukocyte/basophil Measurement Mode

In this measurement mode, blood of 18 $\mu$l and Stromatolyzer FB (II) (manufactured by Sysmex Corporation) of 882 $\mu$l are introduced in the reaction chamber 51. The reaction is continued in this state for about 14 seconds, thereby the erythrocytes are hemolyzed and the nuclei of the leukocytes other than the basophils are exposed and shrunk.

Figure 5:
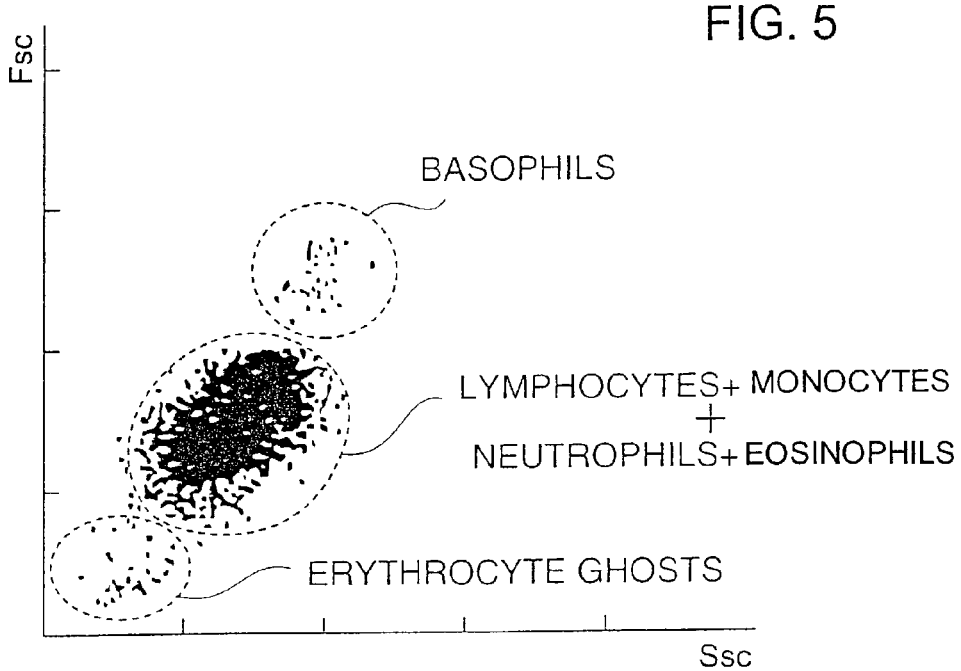
FIG. 5 is an example of a distribution map according to the embodiment of the present invention.

The thus treated sample is discharged from the nozzle 6 by the quantifying syringe 44. Among data obtained by the optical measurement, a side scattered light intensity (Ssc) and a forward scattered light intensity (Fsc) are used to prepare a two-dimensional frequency distribution map of FIG. 5. In FIG. 5, a cluster of basophils and a cluster of lymphocytes, monocytes, neutrophils and eosinophils are respectively classified.

Leukocyte 4-part Differential Measurement Mode

In this measurement mode, blood of 18 $\mu$l and Stromatolyzer 4DL hemolytic agent (manufactured by Sysmex Corporation) of 882 $\mu$l are introduced in the reaction chamber 52. Then, Stromatolyzer 4DS fluorescent stain solution (manufactured by Sysmex Corporation) of 18 $\mu$l is added. The reaction is continued in this state for about 22 seconds to hemolyze the erythrocytes and stain the leukocytes.

Figure 6:
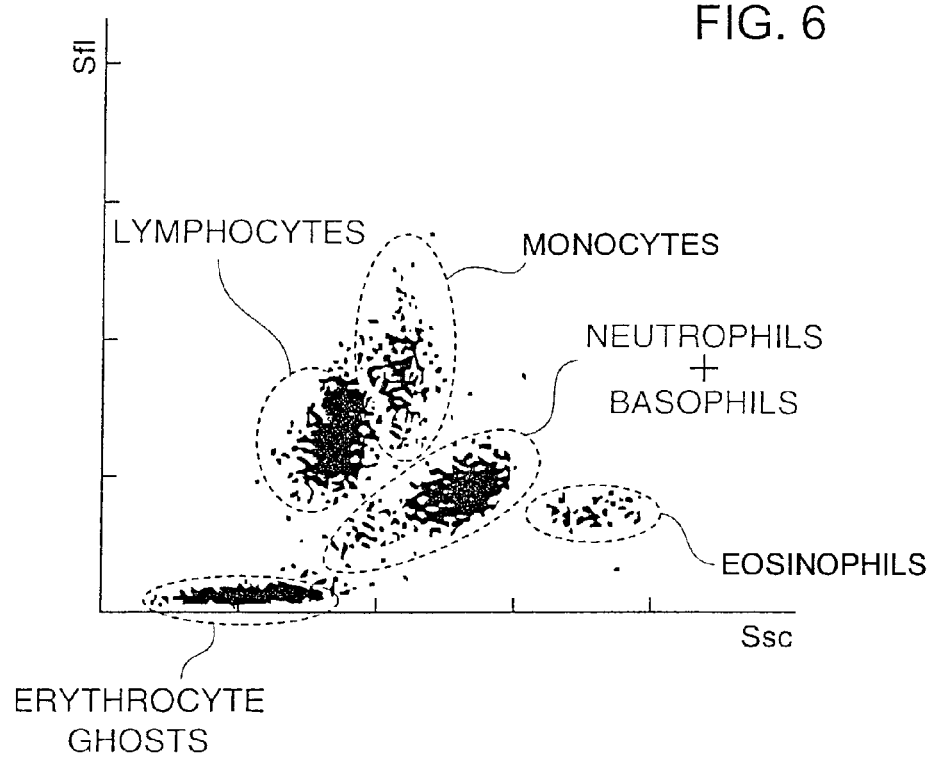
FIG. 6 is an example of a distribution map according to the embodiment of the present invention.

The thus treated blood sample is discharged from the nozzle 6 by the quantifying syringe 44. Among data obtained by the optical measurement, a side scattered light intensity (Ssc) and a side fluorescent light intensity (Sfl) are used to prepare a two-dimensional frequency distribution map of FIG. 6. In FIG. 6, a cluster of lymphocytes, a cluster of monocytes, a cluster of neutrophils and basophils and a cluster of eosinophils are respectively classified.

Reticulocyte Measurement Mode

In this measurement mode, blood of 4.5 $\mu$l and Retsearch (II) diluent (manufactured by Sysmex Corporation) of 895.5 $\mu$l are introduced in the reaction chamber 53. Then, Retsearch (II) fluorescent stain solution (manufactured by Sysmex Corporation) of 18 $\mu$l is added. The reaction is continued in this state for 31 seconds to stain the reticulocytes and the like.

Figure 7:
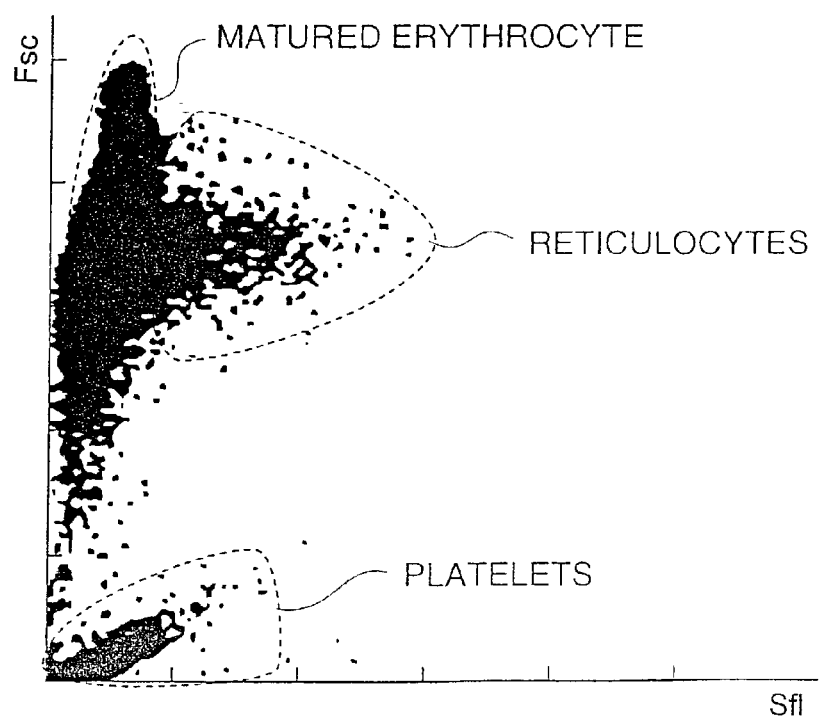
FIG. 7 is an example of a distribution map according to the embodiment of the present invention.

The thus treated blood sample is discharged from the nozzle 6 by the quantifying syringe 44. Among data obtained by the optical measurement, a side fluorescent light intensity (Sfl) and a forward scattered light intensity (Fsc) are used to prepare a two-dimensional frequency distribution map of FIG. 7. In FIG. 7, a cluster of reticulocytes, a cluster of matured erythrocytes and a cluster of platelets are respectively classified.

Figure 9:
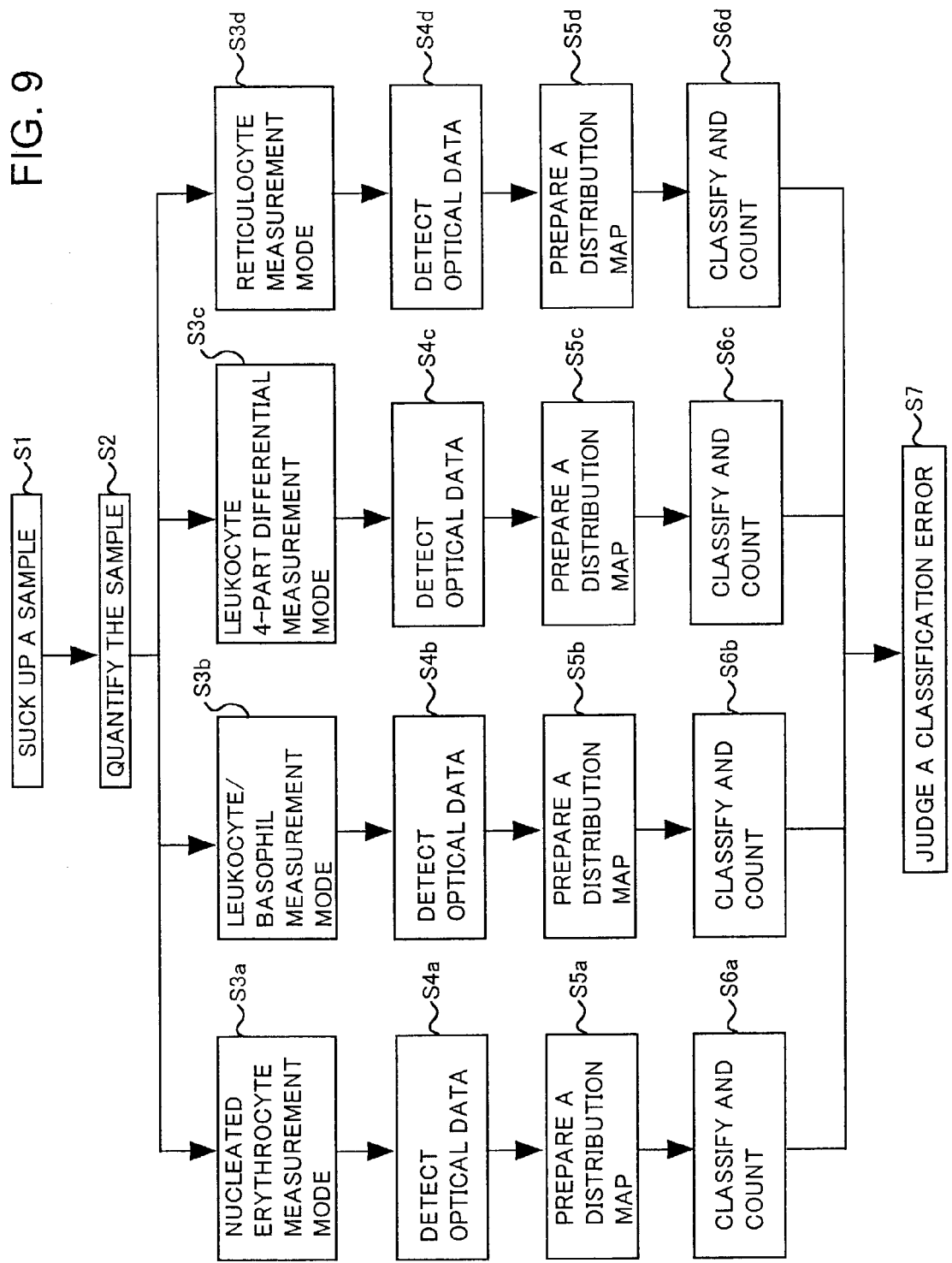
FIG. 9 is a flow chart illustrating the operations of the blood analyzer according to the present invention.

FIG. 9 is a flow chart illustrating the operations of the blood analyzer according to the present invention. This flow chart intelligibly explains the whole process of the above-described sample preparation and measurement as follows.

Step S1: suck up blood collected from a patient;

Step S2: quantify the required amount of the blood for each measurement mode and distribute the blood into the reaction chambers;

Steps S3a to S3d: add predetermined reagents such as a diluent, a stain solution and a hemolytic agent to the quantified blood to react the reagents with the samples, thereby preparing samples each corresponding to the measurement modes (the nucleated erythrocyte measurement mode, the leukocyte/basophil measurement mode, the leukocyte 4-part differential measurement mode and the reticulocyte measurement mode);

Step S4a to S4d: transfer the samples prepared for the measurement modes in sequence to the detecting section to detect optical data by the detecting section;

Step S5a to S5d: prepare two-dimensional frequency distribution maps corresponding to the measurement modes according to the detected optical data;

Step S6a to S6d: classify particles appeared on the distribution maps and count the particles by kind;

Step S7: judge the presence or absence of a classification error by results of the classification and count of the particles on the distribution maps (detailed below).

Judgment of Classification Error

In this embodiment, a single sample is subjected to the nucleated erythrocyte measurement mode, the leukocyte/basophil measurement mode and the leukocyte 4-part differential measurement mode. After the distribution maps shown in FIGS. 4 to 6 are obtained, the calculating section 67 and the judging section 70 (FIG. 3) judge a classification error by the following procedure.

First, the number N1 of the leukocytes and the number N2 of the nucleated erythrocytes are calculated from the distribution map of the nucleated erythrocyte measurement mode shown in FIG. 4. Then, a judgment is made whether or not the following formula is satisfied:

$$100 \times N1/(N1+N2) < 10 \tag{1}$$

If the formula (1) is satisfied, that is, N1 is less than 10%, it means that the number N2 of the nucleated erythrocytes is extraordinarily larger than the number N1 of the leukocytes. This shows the possibility that the sample is collected from a patient who is in poor health or the distribution map of FIG. 4 includes a classification error caused by falsely classifying the leukocytes as the nucleated erythrocytes. Therefore, it is difficult to judge a classification error in the nucleated erythrocyte measurement mode only by the formula (1).

Then, by using both the nucleated erythrocyte measurement mode and the leukocyte 4-part differential measurement mode, the judgment of the classification error is carried out as follows.

Regarding a sample containing the nucleated erythrocytes, the nucleated erythrocytes will appear in a lymphocyte region and a region below the lymphocyte region in the distribution map of the leukocyte 4-part differential measurement mode shown in FIG. 6. Therefore, the sum N3 of the numbers of the neutrophils/basophils and the eosinophils that are classified separately from the above-described regions without containing the nucleated erythrocytes is calculated to compare with the number N1 of the leukocytes obtained from FIG. 4.

Then, if the following formula:

$$N3 > N1 \tag{2}$$

is satisfied, it means that the number N1 of the leukocytes shown in FIG. 4 is smaller than the number N3 of the neutrophils, basophils and eosinophils, which are subclasses of the leukocytes of FIG. 6. This is contradictory and shows the classification error. That is, the formula (2) is a condition that indicates that a major part of the leukocytes is falsely classified as the nucleated erythrocytes in FIG. 4.

If the number N3 of the neutrophils, basophils and eosinophils is considerably low compared with the number of the leukocytes and nucleated erythrocytes, the reliability of the formula (2) is reduced.

When a sample containing a large number of nucleated erythrocytes is measured, the nucleated erythrocytes appear in the region of basophils and the region of lymphocytes, monocytes, neutrophils and eosinophils on the distribution map of the leukocyte/basophil measurement mode shown in FIG. 5. Therefore, the particle number N4 in the region of basophils which may contain the nucleated erythrocytes and the region of lymphocytes, monocytes, neutrophils and eosinophils on the distribution map of FIG. 5 is counted to be compared by the following formula with the particle number N3 in the cluster of neutrophils, basophils and eosinophils on the distribution map of the leuckocyte 4-part differential measurement mode shown in FIG. 6.

$$100 \times N3/N4 > 10 \tag{3}$$

When the formulae (3) is not satisfied, the judgment due to the formula (2) is not carried out. When the judging section 70 judges the classification error on the distribution map of the nucleated erythrocytes shown in FIG. 4, judgment results are shown in the display section 68.

According to the present invention, the classification error can easily be judged in the particle analyzer for analyzing particles by classifying them on a distribution map. Therefore, false analysis is prevented and analysis precision is improved.

What is claimed is:

1. A particle analyzer including a cytometer comprising:
   a detector for detecting a first characteristic parameter, a second characteristic parameter and a third characteristic parameter from particles in a liquid sample being analyzed;
   first classifying means for classifying particles in the liquid sample into leukocytes and other particles based on the first and second characteristic parameters;
   second classifying means for classifying the leukocytes in the liquid sample into a plurality of subclasses based on the second and third characteristic parameters;
   first calculating means for calculating the number N of particles in all of the leukocytes classified by the first classifying means;
   second calculating means for selecting certain specific subclasses from the plurality of subclasses of leukocytes, for calculating the number of particles in the specific subclasses, and for obtaining the sum M of the numbers of the particles in the specific subclasses;
   means for comparing the number N with the sum M; and
   means for determining that a classification error exists if N<M.

2. A particle analyzer according to claim 1, wherein the plurality of subclasses of leukocytes include a first subclass, a second subclass, a third subclass, and a fourth subclass, and the specific subclasses include the first subclass and the second subclass.

3. A particle analyzer according to claim 2, wherein the first subclass includes eosinophils and the second subclass includes neutrophils and basophils.

4. A particle analyzer according to claim 1, wherein the plurality of subclasses include a first subclass, a second subclass, a third subclass, a fourth subclass, and a fifth subclass.

5. A particle analyzer according to claim 1, wherein the first characteristic parameter includes forward scattered light data, the second characteristic parameter includes side fluorescent light data and the third characteristic parameter includes side scattered light data.

6. A particle analyzer according to claim 5, wherein the forward scattered light data is forward scattered light intensity, the side scattered light data is side scattered light intensity and the side fluorescent light data is side fluorescent light intensity.

7. A particle analyzer according to claim 1, wherein the number of specific subclasses is less than said plurality of subclasses classified by said second classifying means.

8. A particle analyzer according to claim 1, further comprising a distribution map preparing means for preparing a first two-dimensional frequency distribution map based on the first and second characteristic parameters and a second two-dimensional frequency distribution map based on the second and third characteristic parameters, the first classifying means classifying the particles in the liquid sample into the leukocytes and the other particles based on the first two-dimensional frequency distribution map and the second classifying means classifying leukocytes in the liquid sample into the plurality of subclasses based on the second two-dimensional frequency distribution map.

9. A particle analyzer according to claim 8, wherein the first characteristic parameter comprises forward scattered light intensity, the second characteristic parameter comprises side fluorescent light intensity, and third characteristic parameter comprises side scattered light intensity.

10. A particle analyzer according to claim 1 wherein the liquid sample comprises a blood sample.

* * * * *